United States Patent [19]

Tam

[11] Patent Number: 5,446,776

[45] Date of Patent: Aug. 29, 1995

[54] TOMOGRAPHY WITH GENERATION OF RADON DATA ON POLAR GRID POINTS

[75] Inventor: Kwok C. Tam, Schenectady, N.Y.

[73] Assignee: General Electric Company, Schenectady, N.Y.

[21] Appl. No.: 100,818

[22] Filed: Aug. 2, 1993

[51] Int. Cl.⁶ ..................... A61B 6/03; G01N 23/083
[52] U.S. Cl. ......................................... 378/4; 378/901; 378/15; 364/413.16; 364/413.19
[58] Field of Search ................ 378/901, 4, 11, 12, 378/13, 14, 15; 364/413.14, 413.15, 413.16, 413.17, 413.18, 413.19, 413.20, 413.21

[56] References Cited

U.S. PATENT DOCUMENTS

| | | | |
|---|---|---|---|
| 4,920,491 | 4/1990 | Eberhard et al. | 364/413.19 |
| 5,032,990 | 7/1991 | Eberhard et al. | 364/413.15 |
| 5,053,958 | 10/1991 | Tam | 364/413.13 |
| 5,068,882 | 11/1991 | Eberhard | 378/4 |
| 5,073,910 | 12/1991 | Eberhard | 378/4 |
| 5,257,183 | 10/1993 | Tam | 364/413.19 |
| 5,365,560 | 11/1994 | Tam | 378/8 |
| 5,404,293 | 4/1995 | Weng et al. | 364/413.19 |

OTHER PUBLICATIONS

"An Inversion Formula for Cone-Beam Recopnstruction", by H. K. Tuy, Siam J. Appl. Math., vol. 43, No. 3, Jun. 1993, pp. 546–552.

"Convolutional Reconstruction From Cone-Beam Projection Data," by G. N. Minerbo, IEEE Transaction on Nuclear Science, vol. NS-26, No. 2, Apr. 1979, pp. 2682–2684.

"Practical Cone-Beam Algorithm", by Feldkamp et al., J. Opt. Soc. Am. A/vol. 1, No. 6, Jun. 194, pp. 612–619.

"Iterative Three-Dimensional Reconstruction from Twin-Cone Beam Projectsion", by M. Schlindwein, IEEE Transactions on Nuclear Science, vol. NS-25, No. 5, Oct. 1978, pp. 1135–1143.

"Cone-Beam Tomography: Recent Advances and a Tutorial Review", by B. D. Smith, Optical Engineering, vol. 29, No. 5, May 1990, pp. 524–534.

"Image reconstruction from Gone-Beam Projections: Necessary and Sufficient Conditions and Reconstruction Methods", by B. D. Smith, IEEE Transactions on Medical Imaging, vol. MI-4, No. 1, Mar. 1985, pp. 14–25.

"Quantitative Cone-Beam Reconstruction", by Hu et al., SPIE vol. 1092 Medical Imaging III: Image Processing (1989), pp. 492–501.

"Analysis of a 3D Imaging System by Reconstruction from X Radiographies in Conical Geometry", by Pierre Grangeat, Doctoral Thesis, pp. 1–303 No date.

*Primary Examiner*—David P. Porta
*Assistant Examiner*—David Vernon Bruce
*Attorney, Agent, or Firm*—Paul R. Webb, II

[57] ABSTRACT

Computerized tomography provides three-dimensional imaging by applying cone beam energy to an object to be imaged. The energy passes through the object and is detected. The resulting cone beam data is efficiently processed to provide Radon data on polar grid points on a series of vertical planes. The Radon data is calculated by initially defining a Radon circle on each of the coaxial vertical planes. Radon derivative data is calculated at intersection points between the Radon circle and the radial lines. The values of Radon derivative data are binned according to the nearest grid point or nearest two grid points. Values are stored in the bins for each point in a particular plane until values for all of the planes have been supplied. The values for all the points are recalculated with each of a series of source positions, corresponding to the relative positioning of the source of cone beam energy and the object being imaged. Radon derivative data for each particular derivative point within each of the vertical planes is determined by averaging the Radon derivative data supplied to the bin corresponding to the particular point. After this is done for all of the derivative points, integration is performed along the radial lines corresponding to the grid points in order to give the Radon data R at each grid point. The image is then reconstructed based upon the performance of a three-dimensional inverse Radon transform on the Radon data.

15 Claims, 3 Drawing Sheets

TOMOGRAPHY WITH GENERATION OF RADON DATA ON POLAR GRID POINTS

CROSS REFERENCE TO RELATED APPLICATIONS

The invention disclosed and claimed herein is related to the subject matter of the following commonly-assigned patent applications, the entire disclosures of which are hereby incorporated by reference:

Ser. No. 07/631,818, filed Dec. 21, 1990, now abandoned, invented by Kwok C. Tam, entitled "PARALLEL PROCESSING METHOD AND APPARATUS FOR RECONSTRUCTING A THREE-DIMENSIONAL COMPUTERIZED TOMOGRAPHY (CT) IMAGE OF AN OBJECT FROM CONE BEAM PROJECTION DATA OR FROM PLANAR INTEGRAL"; and Ser. No. 07/631,815, filed Dec. 21, 1990, now U.S. Pat. No. 5,257,183, in the name of Kwok C. Tam, entitled "METHOD AND APPARATUS FOR CONVERTING CONE BEAM X-RAY PROJECTION DATA TO PLANAR INTEGRAL AND RECONSTRUCTING A THREE-DIMENSIONAL COMPUTERIZED TOMOGRAPHY (CT) IMAGE OF AN OBJECT".

BACKGROUND OF THE INVENTION

The present invention relates generally to three-dimensional (3D) computerized tomography (CT). More particularly, the present invention relates to tomography where Radon data is generated on polar grid points from cone beam data, the polar grid points being on vertical planes to most efficiently allow conversion to an image, resolution area detector for such imaging and the use of such a detector in a system.

In conventional computerized tomography for both medical and industrial applications, an x-ray fan beam and a linear array detector are used. Two-dimensional (2D) imaging is achieved. While the data set may be complete and image quality is correspondingly high, only a single slice of an object is imaged at a time. When a 3D image is required, a stack of slices approach is employed. Acquiring a 3D data set one 2D slice at a time is inherently slow. Moreover, in medical applications, motion artifacts occur because adjacent slices are not imaged simultaneously. Also, dose utilization is less than optimal because the distance between slices is typically less than the x-ray collimator aperture, resulting in double exposure to many parts of the body. In 2D CT, the scanning path of the source is often a simply circular scan about the object. The linear array detector is fixed relative to the source. (Although it is usual to talk about a scan path of a source relative to the object to be imaged, it is to be appreciated that the object may be rotated or otherwise moved to provide relative motion between the object and the source.)

In a system employing true cone beam geometry for 3D imaging, a cone beam x-ray source and a 2D area detector are used. An object is scanned, preferably over a 360° angular range, either by moving the x-ray source in a scanning circle about the object or by rotating the object while the source remains stationary. In either case, the area detector is fixed relative to the source. The relative movement between the source and object which is to be imaged provides scanning in either case. Compared to the conventional 2D stack of slices approach to achieve 3D imaging, the cone beam geometry has the potential to achieve rapid 3D imaging of both medical and industrial objects with improved dose utilization.

The 3D Ct imaging generally uses a Radon transform approach. The object is defined in terms of its x-ray attenuation coefficient. The measured cone beam projection data corresponds to a line integral of this function over the radial direction from the radiation source to a particular detector element within the detector array. The 3D Radon transform of an object at a point is given by the area integral of the x-ray attenuation coefficient over the plane passing through the point, which plane is perpendicular to the line from the origin to the particular point. If parallel beams of x-rays are applied to the object which is to be imaged, line integrals of the detector data area equal to the Radon transform of the object. However, obtaining the Radon transform is significantly more complex where a cone beam of x-ray or other imaging energy is applied to the object. In that case, obtaining the Radon transform, also called Radon data, is significantly more difficult. Once Radon data is obtained, an inverse Radon transformation is used to convert the Radon data into a reconstructed image which is then displayed.

The present inventor's previous application Ser. No. 07/631,815, incorporated by reference above, discloses a technique for calculating the radial derivative of Radon data from cone beam data. The present inventor's incorporated by reference application Ser. No. 07/631,818 discloses a technique for inverting the Radon data to obtain the reconstructed image of the object which is being viewed. In order to perform the Radon inversion, Radon data (as opposed to derivatives of Radon data) is required (except where using those few processors which perform Radon inversion using derivative data) and the Radon data should reside on polar grids on a number of predetermined vertical planes containing the Z axis as the common axis. These requirements arise because the first part of the Radon inversion process is a two dimensional (2D) CT image reconstruction on each vertical plane, which takes input data in the form of Radon data at equally spaced angle Θ and equally spaced detector spacings s. However, the technique of the referenced Ser. No. 07/631,815 application initially produces radial derivatives of the Radon data, instead of Radon data itself, and the derivative data is generated on a spherical shell having as its diameter a line segment SO connecting a source position S and an origin O (instead of being generated on the points of the polar grids). The Ser. No. 07/631,815 application further describes techniques for converting from the radial derivative of Radon data to Radon data itself and to obtain the Radon data on the polar grid points by use of the Radon data relative to the spherical shell, often called the Radon shell However, the calculation of Radon data over the spherical Radon shell requires a relatively large amount of processing or computational power. Further, using that Radon data to provide Radon data at the points on the polar grid of the vertical planes requires relatively complex techniques which, in effect, involve interpolation of different data points on the Radon shell over the shell. This 3D interpolation is relatively complex and it also introduces inaccuracy.

OBJECTS AND SUMMARY OF THE INVENTION

Accordingly, it is a primary object of the present invention to provide a new and improved tomography system and method.

A more specific object of the present invention is to provide three dimensional computerized tomography with a reduced need for computational power.

Yet another object of the present invention is to provide a tomography technique for generating Radon data more efficiently on polar grid points.

Yet another object of the present invention is to provide a tomography technique which avoids the need for three dimensional interpolation.

The above and other objects of the present invention which will become more apparent as the description proceeds are realized by a method of three-dimensional computerized tomography including the steps, not necessarily in order, of generating cone beam imaging energy; passing the cone beam imaging energy through an object of interest; and detecting the cone beam imaging energy as attenuated by passage through the object of interest (may be a medical patient) to provide cone beam data. Next, polar grid points on radial lines of a plurality of coaxial planes are defined, the polar grid points corresponding to points for which Radon data is sought. A Radon circle is defined on each of the plurality of planes. Radon derivative data is calculated using the cone beam data at each point of intersection between the Radon circle on a particular one of the planes and the radial lines. The Radon derivative data is stored in a function bin (i.e., storage location) corresponding to each of a plurality of derivative points on the radial lines of a particular plane. The calculating and storing of Radon derivative data is repeated for each of the planes. The calculating and storing of Radon derivative data is repeated for different relative positions of a source of the cone beam imaging energy and the object of interest until all relative positions for data acquisition have been utilized, each of the planes being used for each of the different relative positions. Upon completion of storage of Radon derivative data in function bins for the derivative points, the values stored in the function bins are used to provide reconstructed image data. An image of the object of interest is then displayed using the reconstructed image data. A further step is the storing of weight data in weight bins, each weight bin corresponding to one of the derivative points, the weight data indicative of the number (may include fractional contributions) of contributions to a function bin corresponding to the weight bin. The Radon derivative data is stored by accumulating a running sum in each function bin and the weight data is stored by accumulating a running sum in each weight bin. The using of the values in the function bins includes the subset of, for each derivative point, dividing the value in the corresponding function bin by the value in the corresponding weight bin to yield R', the Radon derivative data at that derivative point. The using of values in the function bins includes integrating R' to yield R, Radon data, at each grid point; and using R to be reconstructed image data. The step of defining a Radon circle for each plane defines the Radon circle as the intersection of that plane with a spherical Radon shell having a line from the source to an origin as a diameter, the origin being an origin used for defining the Radon data. The calculating and storing of Radon derivative data is performed for a particular plane and relative position of the source, then these steps are repeated for other planes with the same relative position of the source before repeating these steps for the planes with a different relative position of the source.

The system of the present invention is a system for three-dimensional computerized tomography including a source for generating cone beam imaging energy passing it through an object of interest, a detector for detecting the cone beam imaging energy as attenuated by passage through the object of interest to provide cone beam data; and means for defining polar grid points on radial lines on a plurality of coaxial planes for which Radon data is sought. The system further includes means for defining a Radon circle on each of the plurality of planes and means for calculating Radon derivative data using the cone beam data at each point of intersection between the Radon circle and the radial lines on each of the planes for different relative source positions. Means are provided for storing the Radon derivative data in a function bin corresponding to each of a plurality of derivative points on the radial lines on the planes for different relative source positions. Means are provided for, upon completion of storage of Radon derivative data in function bins for the plurality of derivative points, using the values stored in the function bins to provide reconstructed image data. A display is connected to the means for using the values stored in the function bins for displaying an image of the object of interest using the reconstructed image data. Means are provided for storing weight data in weight bins, each weight bin corresponding to one of the derivative points, the weight data indicative of the number of contributions to a function bin corresponding to the weight bin. The number of contributions may include fractions or may be whole numbers. The means for storing the Radon derivative data stores by accumulating a running sum in each function bin. The means for storing weight data stores by accumulating a running sum in each weight bin. The means for using the values stored in the function bins operates, for each derivative point, to divide the value in the corresponding function bin by the value in the corresponding weight bin to yield R', the Radon derivative data of that derivative point.

BRIEF DESCRIPTION OF THE DRAWINGS

The above and other features of the present invention will be more readily understood when the following detailed description is considered in conjunction with the accompanying drawings wherein like characters represent like parts throughout the several views and in which.

DETAILED DESCRIPTION

Figure 1:
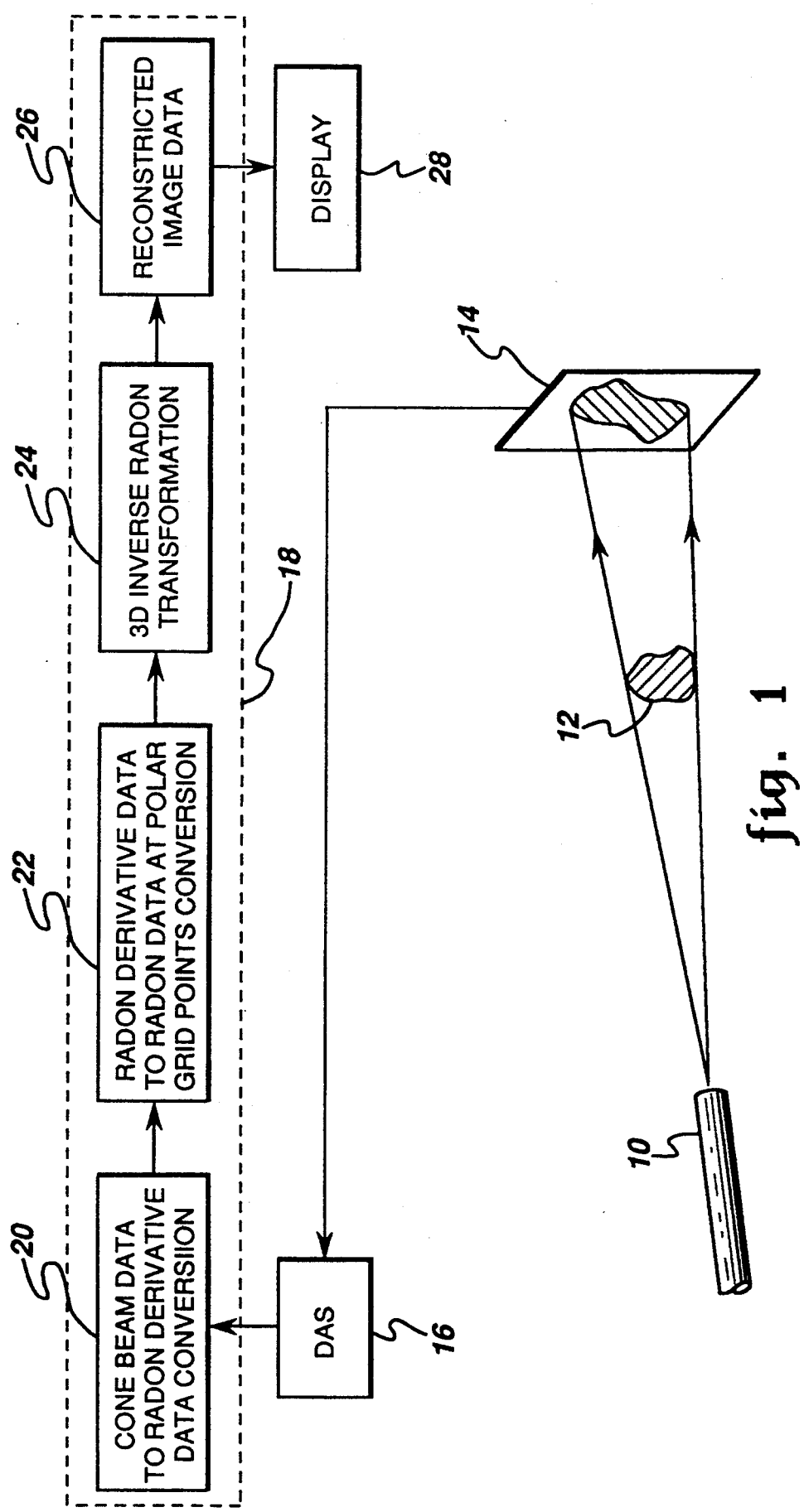
FIG. 1 is a simplified perspective of the imaging of an object using a source and detector and combined with a simplified block diagram of image reconstruction.

As shown in FIG. 1, a cone beam x-ray source 10 generates cone beam energy which passes through and about an object 12 which is to be imaged. Although source 10 is shown as an x-ray source, other types of imaging energy might be used. The imaging energy of whatever type is detected by detector 14. Although individual detector elements are now shown, it will be readily understood that the detector 14 is an array of individual detector elements. Relative movement between the source 10 and object 12 is used to provide more complete data about the object 12. For example, the object 12 could be rotated about a vertical axis (not shown) centered about the object 12. Alternately, and equivalently, the source 10 and detector 14 could be rotated about such an axis, while the object 12 remains stationary. Generally, the source 10 and detector 14 are fixed relative to each other. Additionally, the relative motion between the source 10 and object 12 may be more complex than a simple rotation as various techniques have been developed to insure that a complete data set relative to the object 12 is obtained. Various other techniques provide supplementary data so as to provide reasonably accurate imaging even in cases of incomplete cone beam data. Both of those types of known techniques need not be described in detail for explaining the present invention.

Signals corresponding to the sensed x-ray energy falling on elements within the detector 14 are supplied to data acquisition system 16 which, like the previously described portions of FIG. 1, may operate in known fashion.

Cone beam data from the data acquisition system 16 is supplied to a processor 18, which may be a computer programmed to perform various data conversions illustrated by the blocks within the processor 18. Specifically, the cone beam data is converted to Radon derivative data at block 20. This may be accomplished using the techniques described in the incorporated by reference application Ser. No. 07/631,815. The Radon derivative data is converted to Radon data at polar grid points at block 22 and using a technique which will be discussed in more detail below. The Radon data at the polar grid points is supplied to block 24 which performs an inverse 3D Radon transformation using the techniques described in detail in the incorporated by reference application Ser. No. 07/631,818. Advantageously, the technique used at block 22 bridges the gap between the processes of blocks 20 and 24. A key feature of the present invention is the technique of block 22 which converts the derivative of the Radon data into Radon data in such a way that the data falls exactly on a set of predetermined (usually vertical) planes and the data on each plane falls exactly on polar grid points. Since the technique of block 24 described in detail in the incorporated by reference application Ser. No. 07/631,818 operates on Radon data which is on polar grid points of the set of predetermined vertical planes, block 22 advantageously prepares the data for most efficient use. Additionally, block 22 will perform this processing in a relatively simple manner without requiring calculations of Radon data or Radon derivative data at a large number of points not necessary for the later calculations. Further, the technique of block 22 as described in detail below will avoid three dimensional interpolation and simplify the process for obtaining Radon data at the polar grid points.

The processor 18 supplies reconstructed image data at block 26 from the inverse Radon transformation of block 24. The image data of block 26 are fed from the processor 18 to a display 28, which may operate in known fashion to provide 3D CT imaging of the object 12.

Figure 2:
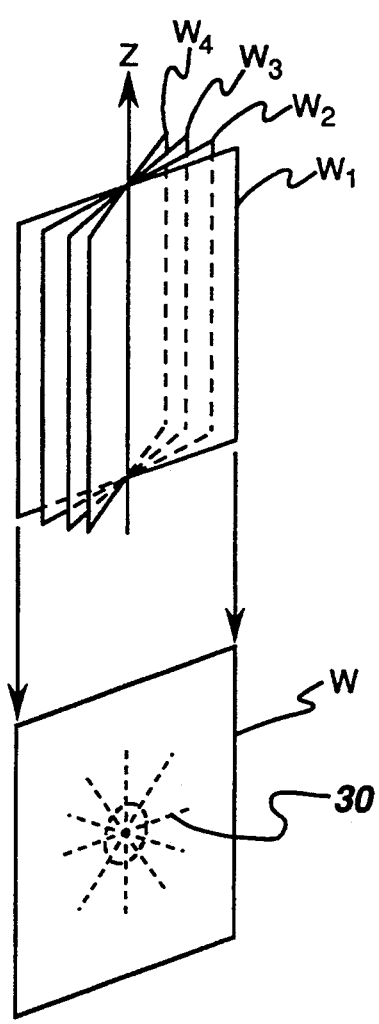
FIG. 2 shows a set of coaxial planes in Radon space, each containing a vertical or reference axis on which Radon data is to be determined, and showing one such plane having polar grid points on which Radon data is to be determined.

With reference now to FIG. 2, a series of vertical planes $W_1$ through $W_4$ are shown, each angularly offset from the other and having a Z axis disposed therein. Although not shown for ease of illustration, the planes may extend at uniform angle separations completely around the Z axis. For example, there could be 90 such planes, each separated from adjacent planes by 2°. Each plane extends on two sides of the Z axis. The lower part of FIG. 2 shows a more detailed view of a particular one of the planes, which has simply been labeled as W. As shown for the plane W, a polar grid 30 is disposed thereon. Similar such polar grids, not shown, would be on each of the vertical planes $W_1$ through $W_n$ where n is the total number of planes. As explained in more detail in the incorporated by reference applications, the Radon data should be determined on the polar grid points of polar grid 30 for each of the vertical planes in order to perform the inverse Radon transformation in accord with the techniques described in those two applications. A technique for very advantageously obtaining that Radon data on those polar grid points will now be described.

Figure 3:
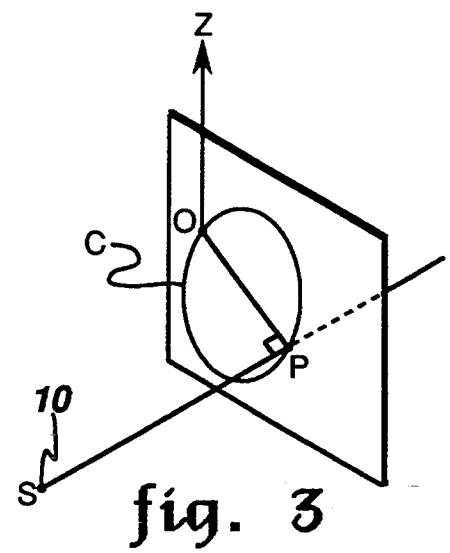
FIG. 3 shows a vertical plane and the source to illustrate how a circle is constructed on the plane for determining points.

Turning to FIG. 3, the Z axis extends from an origin O and the vertical plane W, in which the Z axis is disposed, are illustrated. Additionally, the source 10 is also shown. A line SP is drawn from the source 10 to a point P disposed in plane W, the line being perpendicular to the plane W. A circle C is constructed on the plane W with the line OP as a diameter, this line extending from the origin O to the point P at which a perpendicular line from source S intersects the plane W. The circle C will be referred to as the Radon circle on the plane W. This circle C lies in plane W and is the intersection between a spherical Radon shell (not shown) having line OS (not shown, from origin O to source S) as a diameter and plane W.

Figure 4:
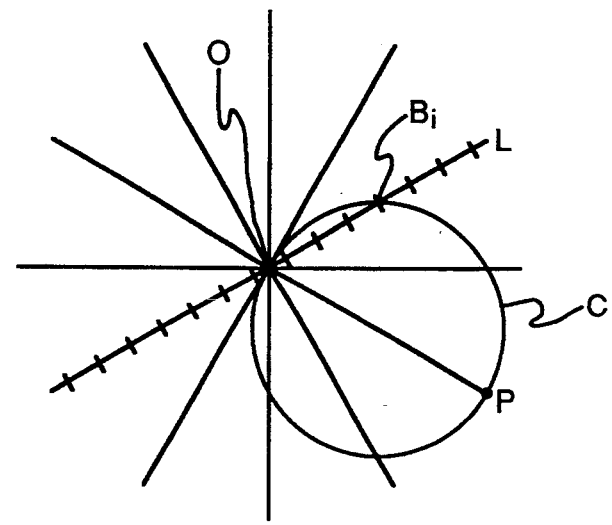
FIG. 4 shows the vertical plane of FIG. 3 with a polar grid superimposed thereon.

Turning now to FIG. 4, there is shown a view of the plane W with the circle C and origin O with the polar grid disposed thereon. The polar grid consists of a series of points extending radially outward from the origin O. For ease of illustration, the points are illustrated only by marks along a particular line L, but it will be readily understood that such points would be disposed along each of the illustrated radially extending lines. As illustrated, the circle C intersects the line L at point $B_i$. Since the point $B_i$ is located on the Radon circle C, the derivative of the Radon datum at it can be generated using the technique described in application Ser. No. 07/631,815.

Figure 5:
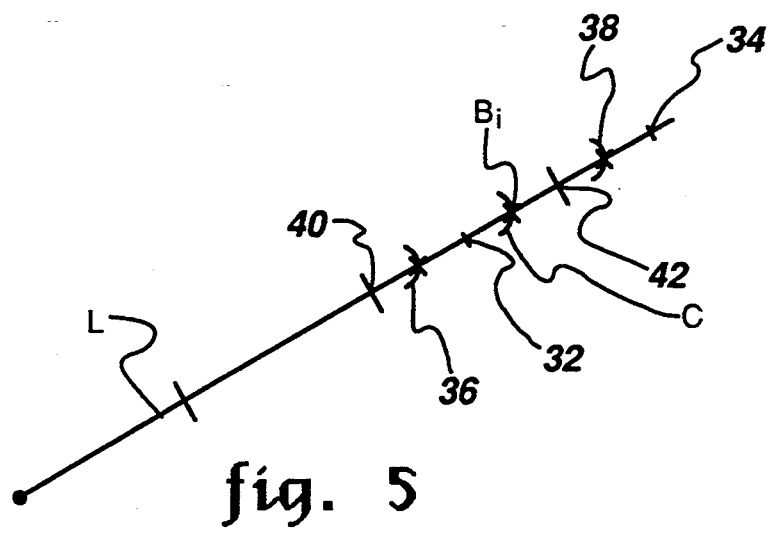
FIG. 5 shows a detailed view of one of the lines on the polar grid of FIG. 4.

The manner in which the Radon derivative data is used will be explained with reference to FIG. 5. FIG. 5 shows the line L with the Radon data points marked thereon. Those points correspond to the location for which Radon data is desired. In order to obtain Radon data at those points, it is best to have the derivative data at the derivative points indicated halfway between adjacent Radon data points. For ease of illustration, only two of the derivative points are shown, but it will be readily understood that one such derivative point would be disposed midway between each two pairs of adjacent Radon data points. For illustrative purposes the Radon data points are shown as longer hash marks than the derivative data points. The intersections between circles and line L are shown with "X" marks. As illustrated, a portion of the circle C passes through the line L at point $B_i$. That point $B_i$ is closest to a derivative point 32 and is disposed between derivative point 32 and a derivative point 34. In order to process the Radon derivative datum determined relative to point $B_i$ using the technique of the incorporated by reference application, a function bin or storage location for derivative values will be established for each derivative point, such as derivative points 32 and 34. Since the derivative datum at point $B_i$ is in between derivative points 32 and 34, a fraction of the value of the Radon derivative at point $B_i$ will be assigned to the two function bins on line L which are closest to point $B_i$ using a suitable weighting. An example may be useful for explaining this process. Assume that the derivative of the Radon datum at point $B_i$ is determined to be 4 and that point $B_i$ is separated from point 34 by ¾ of the distance separating points 32 and 34. The bin associated with point 34 could store ¼ of the derivative data value of 4, whereas the bin associated with point 32 might store ¾ of the derivative data since it is much closer to point $B_i$. In other words, the fraction of the derivative data assigned to a particular bin would be determined proportional to the separation distance between the place of the actual derivative calculation ($B_i$) and the other derivative point. Thus, a derivative datum of 4 at $B_i$ would result in a storage of 3 at the bin associated with point 32 and a storage of a value of 1 at the bin associated with point 34. If the point $B_i$ was separated from point 34 by 4/5 of the separation distance between points 32 and 34, 4/5 of the value calculated at point $B_i$ would be allocated to the bin associated with 32. If the point $B_i$ falls exactly on point 32, 100% of the derivative datum calculated for $B_i$ would be allocated to the bin associated with point 32.

Although the weighting of the derivative datum may include fractions as discussed with the example above, the most simple technique for weighting the Radon derivative data is the nearest-neighbor scheme or technique. In that case, the Radon derivative datum associated with point $B_i$ would be allocated to the bin corresponding to point 32 since point $B_i$ is closer to point 32 than it is to any other derivative point on the line L. When using such a nearest-neighbor scheme, the fraction of the derivative datum assigned to the bin corresponding to a point such as 34 would be zero. Accordingly, as used herein, assigning a fraction or portion of the Radon derivative data shall include the case of assigning a 100% portion to the nearest derivative point and a 0% portion to the second closest derivative point.

If the value assigned to the kth function bin is f(k), the fraction (1 in the nearest neighbor scheme, ¾ and ¼ respectively for bins corresponding to points 32 and 34 in the first example) assigned to that bin (i.e., associated with the particular derivative point such as points 32 and 34) will be referred to as w(k) and would be stored in a weight bin or storage location. For each of the points, such as points 32 and 34, for which derivative data is desired, there would be corresponding bins or storage locations for values of f and w which would be accumulated. The reason for the accumulation may be understood with reference momentarily back to FIG. 3. The Radon circle C depends on the location of the source S. Recalling that the source moves to different locations, it will intersect the plane W at different points within the plane W. Therefore, there would be a series of such Radon circles (only one shown in FIG. 3). Referring back now to FIG. 5, arc 36 corresponds to another Radon circle within the plane W and arc 38 likewise is a portion of a Radon circle appearing in that same plane. Each of the circles corresponding to circle C and arcs 36 and 38 relate to different source position locations. Since the arc 36 intersects line L closest to Radon derivative point 32, the Radon derivative datum calculated at that intersection point would be allocated at least partly to the bin corresponding to point 32. Assuming that the nearest-neighbor scheme is being used, all of the value of derivative data at the intersection point between arc 36 and line L would be assigned to the bin associated with 32. In similar fashion, the nearest-neighbor scheme would provide that all of the value of Radon derivative datum associated with the intersection of arc 38 and line L would be assigned to the bin corresponding to point 34.

Considering that the function bin corresponding to point 32 will have received values from circle C and from the circle corresponding to arc 36, a technique must be used in order to avoid duplicate counting of the Radon derivative datum. For example, assume the derivative data at point $B_i$ is 4.0, the derivative datum at the intersection of arc 36 and line L is 3.8 and the nearest-neighbor scheme is being used. The values stored in the bins corresponding to point 32 for f and w respectively would be 4.0 and 1.0 upon using circle C and would be 3.8 and 1.0 respectively upon using the circle corresponding to arc 36. The cumulative value of f would be 7.8 and the cumulative value of w would be 2.0. By dividing the cumulative value of f by the cumulative value of w for a particular point, such as point 32, an average can be obtained. Further, this avoids double-counting of points such as point 32 which are adjacent to numerous of the Radon circles. Thus, dividing the cumulative value of f and w would, in this example, yield a derivative datum of 3.9 at the point 32.

The process described in detail with respect to FIG. 5 would be repeated for all of the lines intersection the circle C of FIG. 4. Like wise, this would be repeated for all of the Radon circles defined in the vertical plane W as the source 10 moves relative to the vertical plane W. For example, assuming that the source 10 moves 360° around in a circle relative to the vertical plane W, a different Radon circle could be defined for each degree of movement. Note that when the source 10 is disposed in the vertical plane W, point S and point P coincide. Assuming that one was using a Radon circle for each 1° in movement around a 360° path, there would be 360 such Radon circles on any particular vertical plane. This same process is performed for each of the vertical planes such as $W_1$, $W_2$ (refer back momentarily to FIG. 2), etc. In practice, the Radon circles for each of the vertical planes might be calculated before performing the calculations for the Radon circles defined for a new position of the source 10 or S. That is, the calculations for a single circle within each vertical plane might be performed before performing calculations for different circles within a plane.

After the derivative of Radon data is calculated for each of the desired derivative points, such as points 32 and 34 in FIG. 5 and for all source positions, the accumulated value of f in each bin is normalized or averaged by dividing it by the corresponding value of w. This yields the averaged radial derivative of the Radon data at the averaged position of each bin.

Continuing to view FIG. 5, once the derivative of the Radon data is determined at the various derivative points, the Radon data itself may be obtained by integrating the computed derivatives along each line in the polar grid. Recalling initially that only the two derivative points 32 and 34 are shown in FIG. 5, but that similar derivative points would be located midway between each pair of adjacent Radon data points, this line integration may be performed in known fashion. However, a brief explanation of such line integration will be presented by use of Radon grid points 40 and 42 assuming that the Radon derivative value has been determined at derivative point 32 using the described technique. The Radon value at point 42 is equal to the Radon value at point 40 added to the quantity of the derivative value at point 32 multiplied by the separation distance between points 40 and 42. The separation distance is a known quantity and the derivative value at point 32 will of course be known from the previous calculations. The Radon value at point 40 (or some other initial starting point) may have been determined initially by boundary value conditions. In other words, knowledge of some initial Radon value from boundary value considerations allows us to use the Radon derivative data to calculate Radon values at other points. Once the Radon value at a point such as point 40 is known, knowledge of that Radon value together with the Radon derivative value at a point such as point 32 is known, the Radon value for a point, radially outwardly disposed from the first Radon point, can be readily calculated. As will be appreciated, this integration process is an approximate integration using a summation of area under a curve.

Once the Radon data is obtained for the polar grid points on the various vertical planes, the inverse Radon transformation can be performed using the techniques described in the incorporated by reference application Ser. No. 07/631,818. Moreover, as described in that application, there are certain processors which allow one to obtain a reconstructed image without initially changing from Radon derivative data into Radon data itself. For such processors, it would be unnecessary to perform the line integration to convert the derivative data into Radon data itself. Generally, however, the Radon derivative data is converted to Radon data before reconstructing the image.

Figure 6:
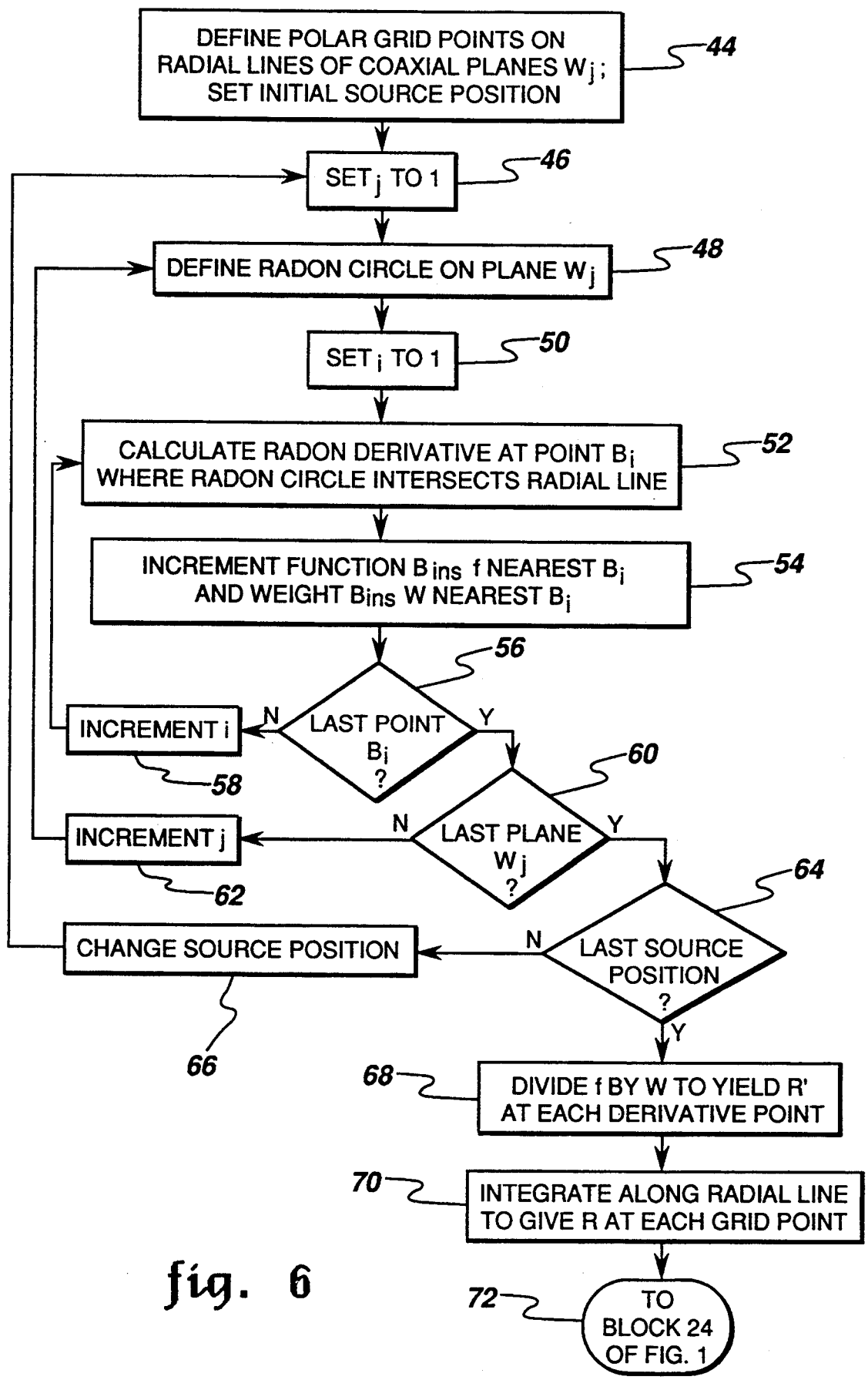
FIG. 6 is a simplified flowchart of part of the present invention.

With reference now to FIG. 6, a simplified flow chart shows more of the details of portions of the operation of processor 18 from FIG. 1. Specifically, the flowchart of FIG. 6 concentrates on steps which are part of block 22 of FIG. 1, but it will be appreciated that portions of this flowchart are steps which conceptually would be part of block 20 in FIG. 1. For example, initial block 44 defines the polar grid points on radial lines of the coaxial planes $W_j$ in the fashion described in detail in connection with the incorporated by reference application Ser. No. 07/631,815, which step may be considered as part of block 20 in FIG. 1. Additionally, block 44 of FIG. 6 involves setting of an initial source position. It should be emphasized that this simply means setting a relative position between the source and the object being imaged. As discussed previously, the object may be fixed relative to a moving source or the source may be fixed and the object may be moved. In either case, block 44 simply indicates that a particular relative positioning of the source and object would be considered as an initial source position for data acquisition.

Block 44 leads to block 46 which initializes a value of j (an integer value used as an index in a do loop) is set to 1. Block 46 leads to block 48 where a Radon circle is defined on the particular plane $W_j$ using the technique described above with respect to FIG. 3. Next, block 50 initializes another do loop index variable, i, to 1. Next, block 52 calculates the Radon derivative at the point $B_i$ where the Radon circle intersects a radial line. With reference momentarily to FIG. 4, point $B_1$ might be considered as the first intersection between the Radon circle C and a radial line upon moving clockwise on the circle from the origin. However, other conventions could be used. As discussed previously, the Radon derivative would be calculated using the techniques described in the incorporated by reference application Ser. No. 07/631,815.

Block 52 leads to block 54 where bins associated with the derivative points as discussed with respect to FIG. 5 would be incremented. Briefly referring back to FIG. 5 for example, the derivative calculated for point $B_i$ would be allocated either completely to a function bin associated with point 32 or a portion of the calculated derivative at point $B_i$ would be allocated to derivative point 32 and the remainder of the calculated derivative value would be allocated to a function bin associated with derivative point 34. A weight bin corresponding to derivative point 32 would be incremented by the fraction of the value of the derivative at point $B_i$ which has been allocated to the function bin associated with point 32. Likewise, the fraction of the value of the derivative at point $B_i$ allocated to the function bin associated with point 34 would be allocated to a weight bin associated with point 34. Again, and as discussed above, if the nearest neighbor scheme is used, all of the derivative value calculated for point $B_i$ would be allocated to the function bin associated with point 32 and a weight of 1 would be placed in the weight bin corresponding to derivative point 32. These function bins and weight bins are incremented in the sense that the current contents of those bins or storage locations are increased in value by the currently calculated amounts. For example, if the current contends of the function and weight bins associated with derivative point 32 are 10.6 and 2 respectively, and the calculation of block 52 yields are derivative value of 5.1, block 54 would increase the function bin by a value of 5.1 such that the function bin would then have a value of 15.7. Assuming that the nearest neighbor technique is being used, the weight bin would be incremented by 1 since all of the calculated derivative value is assigned to the corresponding function bin. Thus, both function values f and weight values w are accumulated as running sums in their respective bins. Note that block 54 refers to the bins nearest point $B_i$, but this of course means the bins corresponding to the derivative points nearest point $B_i$.

Block 54 leads to block 56 which tests to determine if the particular point $B_i$ is the last point of intersection between the Radon circle and the various radial lines on a particular one of the coaxial planes. If it is not the last point, control transfers to block 58 which increments i by 1 and returns control to block 52 such that blocks 52 and 54 repeat their steps for the new point $B_i$. If block 56 determines that the last point of intersection between the Radon circle and the radial lines for that particular plane has been used to provide derivative data, block 56 leads to block 60 which tests to determine if the particular plane $W_j$ is the last plane. If not, block 60 leads to block 62 which increments the value of index variable j by 1 and returns control to block 48 such that calculations may be performed for additional planes.

If block 60 determines that calculations have been performed for the last plane $W_j$, control transfers to block 64 which tests to determine if the last source position has been reached. For example, if the source positions were every 2° throughout a 360° loop of motion between the source and the object being imaged, there would be 180 different source positions. If the process has not been performed yet for the last source position, control transfers to block 66 which changes the source position and begins calculations for the new source position by returning it to block 46. Although block 66 indicates that it changes the source position, the source may be constantly moving relative to the object and block 66 simply indicates that the cone beam data used for calculations is latched onto or stored at a particular time corresponding to one of the source positions. If the source position is the last source position, block 64 proceeds to steps used to calculate the values for the Radon derivative data at the particular derivative points located midway between each of the Radon data points on the radial lines of the vertical plane.

The nesting of the do loops associated with index variables i and j and source position movement may be done in different ways from that illustrated, as will be readily appreciated.

Upon the last source position being reached, block 64 leads specifically to block 68 which divides f, the accumulated sum of function values stored in a bin corresponding to a particular derivative point, by w, the accumulated sum of the weighting values stored in the weight bin corresponding to that particular derivative point, in order to yield R', which is the derivative of the Radon data for that particular derivative point. It will be recalled from the discussion above that each derivative point is midway between adjacent Radon points of the polar grid. Basically, block 68 determines the Radon derivative data by taking an average of the values assigned to a particular function bin in which f has been stored.

If a processor is utilized which can reconstruct image data directly from Radon derivative data, block 68 would lead to such an image reconstruction step as described in more detail in the incorporated by reference application Ser. No. 07/631,818. In the more usual case, and as illustrated in FIG. 6, block 68 leads to block 70 where a line integration is performed along the radial line in order to give R, the Radon data, at each grid point. It will be appreciated that block 70, like block 68 before it, reciters steps which are performed for each relevant point (derivative points for block 68, grid points for block 70) within all of the coaxial planes previously defined by block 44. Block 70 leads to block 72 which simply indicates a return to the block 24 of FIG. 1, whereat the image reconstruction process may be performed in the manner described in the incorporated by reference application Ser. No. 07/631,818.

Although specific constructions and steps have been described herein, it is to be understood that these details are for illustrative purposes only. Various modifications and adaptations will be apparent to those of skill in this art. Accordingly, the scope of the present invention should be determined by reference to the claims appended hereto.

What is claimed is:

1. A method of three-dimensional computerized tomography comprising the steps, not necessarily in order, of:
   (a) generating cone beam imaging energy;
   (b) passing the cone beam imaging energy through an object of interest;
   (c) detecting the cone beam imaging energy as attenuated by passage through the object of interest to provide cone beam data;
   (d) defining polar grid points on radial lines on a plurality of coaxial planes for which Radon data is sought;
   (e) defining a Radon circle on each of said plurality of planes;
   (f) calculating Radon derivative data using said cone beam data at each point of intersection between the Radon circle on a particular one of said planes and said radial lines;
   (g) storing Radon derivative data in a function bin corresponding to each of a plurality of derivative points on said radial lines of a particular plane;
   (h) repeating steps (f) and (g) for each of said planes;
   (i) repeating steps (f) to (h) for different relative positions of a source of said cone beam imaging energy and said object of interest until all relative positions for data acquisition have been utilized;
   (j) upon completion of storage of Radon derivative data in function bins for the plurality of derivative points, using the values stored in the function bins to provide reconstructed image data; and
   (k) displaying an image of the object of interest using said reconstructed image data.

2. The method of claim 1 further comprising storing weight data in weight bins, each weight bin corresponding to one of said derivative points, the weight data indicative of the number of contributions to a function bin corresponding to the weight bin.

3. The method of claim 2 wherein Radon derivative data is stored by accumulating a running sum in each function bin and weight data is stored by accumulating a running sum in each weight bin.

4. The method of claim 3 wherein the using of the values in the function bins includes the substep of:
   for each derivative point, dividing the value in the corresponding function bin by the value in the corresponding weight bin to yield R', the Radon derivative data at that derivative point.

5. The method of claim 4 wherein the using of the values in the function bins includes the substep of:
   integrating R' to yield R, Radon data, at each grid point; and
   using R to provide reconstructed image data.

6. The method of claim 1 wherein said step of defining a Radon circle for each plane defines the Radon circle as the intersection of that plane with a spherical Radon shell having a line from said source to an origin as a diameter, the origin being an origin used for defining the Radon data.

7. The method of claim 6 further comprising storing weight data in weight bins, each weight bin corresponding to one of said derivative points, the weight data indicative of the number of contributions to a function bin corresponding to the weight bin.

8. The method of claim 7 wherein Radon derivative data is stored by accumulating a running sum in each function bin and weight data is stored by accumulating a running sum in each weight bin.

9. The method of claim 8 wherein the using of the values in the function bins includes the substep of:

for each derivative point, dividing the value in the corresponding function bin by the value in the corresponding weight bin to yield R′, the Radon derivative data at that derivative point.

10. The method of claim 9 wherein the using of the values in the function bins includes the substep of:

integrating R′ to yield R, Radon data, at each grid point; and using R to provide reconstructed image data.

11. The method of claim 10 wherein said step of defining a Radon circle for each plane defines the Radon circle as the intersection of that plane with a spherical Radon shell having a line from said source to an origin as a diameter, the origin being an origin used for defining the Radon data.

12. The method of claim 1 wherein steps (f) and (g) are performed for a particular plane and relative position of the source, then steps (f) and (g) are repeated for other planes with the same relative position of the source before repeating (f) and (g) for the planes with a different relative position of the source.

13. A system for three-dimensional computerized tomography comprising:

a source for generating cone beam imaging energy passing it through an object of interest;

a detector for detecting the cone beam imaging energy as attenuated by passage through the object of interest to provide cone beam data;

means for defining polar grid points on radial lines on a plurality of coaxial planes for which Radon data is sought;

means for defining a Radon circle on each of said plurality of planes;

means for calculating Radon derivative data using said cone beam data at each point of intersection between the Radon circle and said radial lines on each of the planes for different relative source positions;

means for storing the Radon derivative data in a function bin corresponding to each of a plurality of derivative points on said radial lines on said planes for different relative source positions;

means for, upon completion of storage of Radon derivative data in function bins for the plurality of derivative points, using the values stored in the function bins to provide reconstructed image data; and a display connected to said means for using the values stored in the function bins for displaying an image of the object of interest using said reconstructed image data.

14. The system of claim 13 further comprising means for storing weight data in weight bins, each weight bin corresponding to one of said derivative points, the weight data indicative of the number of contributions to a function bin corresponding to the weight bin.

15. The system of claim 14 wherein said means for storing Radon derivative data stores by accumulating a running sum in each function bin; said means for storing weight data stores by accumulating a running sum in each weight bin; and wherein said means for using the values stored in the function bins operates, for each derivative point, to divide the value in the corresponding function bin by the value in the corresponding weight bin to yield R′, the Radon derivative data at that derivative point.

* * * * *